(12) United States Patent
Place et al.

(10) Patent No.: US 6,450,953 B1
(45) Date of Patent: Sep. 17, 2002

(54) PORTABLE SIGNAL TRANSFER UNIT

(75) Inventors: John D. Place, Suffolk; Paul Johnson, Oxford; Steven Jones, Bucks; Harpal S. Kumar, Cambridge; William J. Mullarkey, Wigan, all of (GB); William New, Jr., Woodside, CA (US); Laurence J. Nicolson, Liverpool (GB); Peter M. Relph, Essex (GB)

(73) Assignee: Nexan Limited, Cambridge (GB)

( * ) Notice: Subject to any disclaimer, the term of this patent is extended or adjusted under 35 U.S.C. 154(b) by 0 days.

(21) Appl. No.: 09/292,158

(22) Filed: Apr. 15, 1999

(51) Int. Cl.$^7$ .................................................. A61B 5/00
(52) U.S. Cl. ........................ 600/300; 128/903; 600/508
(58) Field of Search .................................. 600/300–301, 600/481–486, 500–508, 529–538, 544–545; 128/903, 904

(56) References Cited

U.S. PATENT DOCUMENTS

| | | |
|---|---|---|
| 2,298,125 A | 10/1942 | Hartman |
| 2,660,165 A | 11/1953 | Miller |
| 3,212,496 A | 10/1965 | Preston |
| 3,409,007 A | 11/1968 | Fuller |
| 3,572,316 A | 3/1971 | Vogelman et al. |
| 3,572,322 A | 3/1971 | Wade |
| 3,603,881 A | 9/1971 | Thornton |
| 3,757,778 A | 9/1973 | Graham |
| 3,848,582 A | 11/1974 | Milani et al. |
| 3,858,576 A | 1/1975 | Dehnert et al. |
| 3,882,277 A | 5/1975 | DePedro et al. |
| 3,902,478 A | 9/1975 | Konopasek et al. |
| 3,908,641 A | 9/1975 | Judson et al. |
| 3,943,918 A | 3/1976 | Lewis |
| 3,986,498 A | 10/1976 | Lewis |
| 4,023,564 A | 5/1977 | Valiquette et al. |
| 4,082,087 A | 4/1978 | Howson |
| 4,121,573 A | 10/1978 | Crovella et al. |
| 4,121,575 A | 10/1978 | Mills et al. |
| 4,122,843 A | 10/1978 | Zdrojkowski |
| 4,141,351 A | 2/1979 | James et al. |
| 4,202,344 A | 5/1980 | Mills et al. |

(List continued on next page.)

FOREIGN PATENT DOCUMENTS

| | | |
|---|---|---|
| CH | 293560 | 12/1953 |
| EP | 0 212 278 | 3/1987 |
| EP | 0 479 857 B1 | 12/1993 |

(List continued on next page.)

OTHER PUBLICATIONS

"Microcomputer–based Telemetry System for ECG Monitoring," *Proceedings of the Ninth Annual Conference of the IEEE Engineering in Medicine and Biology Society*, The Boston Park Plaza Hotel, Boston, MA, Nov. 13–16, 1987, vol. 3 of 4, 2 pages.

(List continued on next page.)

*Primary Examiner*—Robert L. Nasser
*Assistant Examiner*—Micheal Astorino
(74) *Attorney, Agent, or Firm*—Woodcock Washburn Kurtz Mackiewicz & Norris LLP (57) ABSTRACT

A portable signal transfer unit for relaying a signal representative of physiological data of a mammalian subject from a remote physiological sensor to a remote receiver unit. The portable transfer unit includes an input device which operably receives the signal, a memory for buffering the signal, and an output device which wirelessly transmits the signal to the remote unit. The signal transfer unit also includes a signal processor for relaying the signal from the signal input to the output device, wherein the signal processor has two or more receivers each receiver adapted to handle a specified signal carrier frequency. An indicator is also provided which indicates to the subject whether the signal transfer unit is within range of the remote unit to enable effective transmission of the signal from the signal transfer unit to the remote unit.

33 Claims, 5 Drawing Sheets

U.S. PATENT DOCUMENTS

| | | | |
|---|---|---|---|
| 4,220,955 A | * 9/1980 | Frye | 343/703 |
| 4,233,987 A | 11/1980 | Feingold | |
| 4,249,538 A | 2/1981 | Musha et al. | |
| 4,319,241 A | 3/1982 | Mount | |
| 4,328,814 A | 5/1982 | Arkans | |
| 4,353,372 A | 10/1982 | Ayer | |
| 4,356,486 A | 10/1982 | Mount | |
| 4,494,553 A | 1/1985 | Sciarra et al. | |
| 4,522,211 A | 6/1985 | Bare et al. | |
| 4,561,443 A | * 12/1985 | Hogrefe et al. | 128/903 |
| 4,593,284 A | 6/1986 | Clifford et al. | |
| 4,606,352 A | 8/1986 | Geddes et al. | |
| 4,622,979 A | 11/1986 | Katchis et al. | |
| 4,658,831 A | 4/1987 | Reinhard et al. | |
| 4,662,378 A | 5/1987 | Thomis | |
| 4,709,704 A | 12/1987 | Lukasiewicz | |
| 4,742,831 A | 5/1988 | Silivian | |
| 4,763,660 A | 8/1988 | Kroll et al. | |
| 4,784,162 A | 11/1988 | Ricks et al. | |
| 4,803,491 A | * 2/1989 | Hikuma | 343/702 |
| 4,827,943 A | 5/1989 | Bornn et al. | |
| 4,852,572 A | 8/1989 | Nakahashi et al. | |
| 4,893,632 A | 1/1990 | Armington | |
| 4,909,260 A | 3/1990 | Salem et al. | |
| 4,926,868 A | 5/1990 | Larsen | |
| 4,955,381 A | 9/1990 | Way et al. | |
| 4,957,109 A | 9/1990 | Groeger et al. | |
| 4,967,748 A | 11/1990 | Cohen | |
| 4,967,749 A | 11/1990 | Cohen | |
| 4,981,141 A | 1/1991 | Segalowitz | |
| 4,984,572 A | 1/1991 | Cohen | |
| 4,986,270 A | 1/1991 | Cohen | |
| 5,027,816 A | 7/1991 | Cohen | |
| 5,038,782 A | 8/1991 | Gevins et al. | |
| 5,050,612 A | 9/1991 | Matsumura | |
| 5,069,215 A | 12/1991 | Jadvar et al. | |
| 5,078,134 A | 1/1992 | Heilman et al. | |
| 5,080,099 A | 1/1992 | Way et al. | |
| 5,163,429 A | 11/1992 | Cohen | |
| 5,168,874 A | 12/1992 | Segalowitz | |
| 5,199,433 A | 4/1993 | Metzger et al. | |
| 5,224,485 A | 7/1993 | Powers et al. | |
| 5,228,449 A | 7/1993 | Christ et al. | |
| 5,269,301 A | 12/1993 | Cohen | |
| 5,279,305 A | 1/1994 | Zimmerman et al. | |
| 5,307,817 A | 5/1994 | Guggenbuhl et al. | |
| 5,307,818 A | 5/1994 | Segalowitz | |
| 5,343,860 A | 9/1994 | Metzger et al. | |
| 5,353,793 A | 10/1994 | Bornn | |
| 5,372,125 A | 12/1994 | Lyons | |
| 5,373,852 A | 12/1994 | Harrison et al. | |
| 5,394,882 A | 3/1995 | Mawhinney | |
| 5,431,171 A | 7/1995 | Harrison et al. | |
| 5,456,682 A | 10/1995 | Edwards et al. | |
| 5,458,124 A | 10/1995 | Stanko et al. | |
| 5,462,051 A | 10/1995 | Oka et al. | |
| 5,465,098 A | * 11/1995 | Fujisawa et al. | 343/718 |
| 5,465,715 A | 11/1995 | Lyons | |
| 5,511,553 A | 4/1996 | Segalowitz | |
| 5,522,396 A | 6/1996 | Langer et al. | |
| 5,538,005 A | 7/1996 | Harrison et al. | |
| 5,544,661 A | 8/1996 | Davis et al. | |
| 5,549,113 A | 8/1996 | Halleck et al. | |
| 5,558,638 A | 9/1996 | Evers et al. | |
| 5,564,429 A | 10/1996 | Bornn et al. | |
| 5,579,001 A | 11/1996 | Dempsey et al. | |
| 5,579,775 A | 12/1996 | Dempsey et al. | |
| 5,617,871 A | 4/1997 | Burrows | |
| 5,634,468 A | 6/1997 | Platt et al. | |
| 5,652,570 A | 7/1997 | Lepkofker | |
| 5,670,944 A | 9/1997 | Myllymäki | |
| 5,678,545 A | 10/1997 | Stratbucker | |
| 5,682,902 A | 11/1997 | Herleikson | |
| 5,687,734 A | 11/1997 | Dempsey et al. | |
| 5,720,770 A | * 2/1998 | Nappholz et al. | 607/30 |
| 5,771,001 A | 6/1998 | Cobb | |
| 5,862,803 A | 1/1999 | Besson et al. | |
| 5,891,044 A | 4/1999 | Golosarsky et al. | |
| 6,083,248 A | * 7/2000 | Thompson | 607/30 |
| 6,115,636 A | * 9/2000 | Ryan | 607/30 |
| 6,259,355 B1 | * 7/2001 | Chaco et al. | 128/903 |

FOREIGN PATENT DOCUMENTS

| | | |
|---|---|---|
| EP | 0 617 914 A1 | 10/1994 |
| EP | 0 458 883 B1 | 11/1996 |
| EP | 0 760 224 A1 | 3/1997 |
| EP | 0 761 160 A1 | 3/1997 |
| EP | 0 770 349 A1 | 5/1997 |
| EP | 0 719 108 B1 | 6/1997 |
| EP | 0 796 589 A1 | 9/1997 |
| EP | 0 796 590 A1 | 9/1997 |
| EP | 0 598 016 B1 | 10/1997 |
| GB | 2 003 276 A | 3/1979 |
| GB | 2 207 579 A | 2/1989 |
| WO | WO 87/06447 | 11/1987 |
| WO | WO 90/01898 | 3/1990 |
| WO | WO 91/00054 | 1/1991 |
| WO | WO 93/02622 | 2/1993 |
| WO | WO 93/08734 | 5/1993 |
| WO | WO 93/10706 | 6/1993 |
| WO | WO 93/19667 | 10/1993 |
| WO | WO 94/01039 | 1/1994 |
| WO | WO 94/03105 | 2/1994 |
| WO | WO 94/25841 | 11/1994 |
| WO | WO 95/07048 | 3/1995 |
| WO | WO 95/07652 | 3/1995 |
| WO | WO 95/10974 | 4/1995 |
| WO | WO 96/01585 | 1/1996 |
| WO | WO 96/29005 | 9/1996 |
| WO | WO 96/38080 | 12/1996 |
| WO | WO 97/09923 | 3/1997 |
| WO | WO 97/28736 | 8/1997 |
| WO | WO 97/40747 | 11/1997 |

OTHER PUBLICATIONS

"Biomedical Telectrodes: Compact transmitters would eliminate the need for wires to monitors," *NASA TechBrief*, Lyndon B. Johnson Space Center, Houston, Texas, Feb., 1990, 1 page.

* cited by examiner

PORTABLE SIGNAL TRANSFER UNIT

BACKGROUND OF THE INVENTION

1. Field of the Invention

The invention relates to a signal transfer unit for use in a physiological monitoring system. In particular, the invention relates to a portable signal transfer unit enabling transfer of physiological data from a physiological sensor attached to a mammalian subject in use, to a remote base station.

2. Description of the Prior Art

It is known to provide sensors for collecting physiological data from a patient and then to transfer the data from the sensor via wireless transmission to a remote base station unit for signal processing and storage. However, such systems locate the signal transmitter adjacent the sensor and, accordingly, the system as a whole and in particular the transmission unit is required to be lightweight precluding the use of transmission of too strong a signal or any data storage capacity thereby to ensure that the system is lightweight and attachable to the patient.

An example of the prior art includes WO94/01039 which provides a precordial system comprising a strip of sensors for detecting electrocardiographic data.

The system comprises a signal amplifier, encoder modulator and RF transmitter for relaying the data to a base station comprising a receiver module and suitable signal processing equipment to enable a clinician to monitor the cardiac rhythms of the patient. However, the precordial system must carry its own power supply for continuous use in running a transmitter which is capable of sending RF signals of a reasonable distance to the receiving unit. Such systems provide real dangers of losing data from a patient due to interruption in communication of the signal from the precordial system with the remote unit.

SUMMARY OF THE INVENTION

An object of the invention is to avoid or at least mitigate some or all of the problems of the prior art. One object of the invention is to provide a portable signal transfer unit operably in close proximity to or wearable by the patient remote from but proximal a physiological sensor, for example, by attachment to an external item of clothing worn by the patient, such as a belt. Another object is to provide one such unit adapted for use with multiple sensors, for example, located on different parts of a patient's body such as on arms, chest and legs.

According to a first aspect of the invention, there is provided a portable signal transfer unit for relaying a signal representative of physiological data of a mammalian subject from a remote physiological sensor to a remote receiver unit, comprising an input device which operably receives the signal, a memory for buffering the signal and an output device which wirelessly transmits the signal to the remote receiver unit, such as a base station. Beneficially, the signal transfer unit can be somewhat larger than the physiological sensor itself and can be carried in a convenient location on the subject such as attached to a waist belt by using a clip on the signal transfer unit. As a result, sufficient power and memory can be provided within the signal transfer unit to enable relatively long term buffering and/or storage of a signal, for example, over several minutes or even longer than 30 minutes.

Preferably, the signal input device is adapted to receive a wireless transmission and can comprise two or more antennae for receiving the signal, and preferably three antennae are provided. Preferably, the three coils are substantially orthogonally arranged within the signal transfer unit. As a result of this configuration, satisfaction reception is established between the signal transfer unit and the remote physiological sensor.

In one embodiment, the signal input comprises a coil for inductive coupling with a transmission coil on a remote physiological sensor device. Preferably, three orthogonally arranged coils can be provided within the signal transfer unit and electrically conductive screening is provided between at least two of the coils and electrical components within the signal transfer unit, and preferably between each of the coils and electrical components within the signal transfer unit.

The output device can comprise a stub antenna or a plate antenna, for example. Where a plate antenna is used, this may be fairly large and therefore substantially equal to the surface area of the largest face of an outer casing for the signal transfer unit. The plate antenna can comprise a conductive track on a non-conductive substrate such as a copper track on a printed circuit board, for example. Preferably, the plate antenna is positioned adjacent the wall of the casing adapted to be adjacent the subject in use, which wall can for example comprise a clip attachable to a belt.

The signal transfer unit preferably comprises a signal amplifier stage and digital signal processing stage between the signal input and output device. Also, preferably a second input device enabling communication with the controller from a remote unit such as a base station is provided. The second input device can comprise a transceiver enabling both input and output of data and/or commands. For example, the second input device can comprise an RF receiver.

Preferably the units can comprise a subject interface including any one or more of the following: an on/off switch adapted to remove or enable power supply to the unit, an indicator such as a light to indicate the status of the power supply to the unit, an indicator such as a light to indicate whether a signal is being received from the physiological sensor device, an indicator such as a light to provide an indication of whether the unit is within range of the remote unit to enable transfer of the signal, a user output such as an audible alarm operable upon command from the remote unit, and preferably a switch to enable the user to deactivate the user output when appropriate.

The signal transfer unit can comprise a signal processor stage having one or more receivers for handling specified signal carrier frequencies.

According to an aspect of the invention there is provided a signal transfer unit for relaying signals representative of physiological data of a mammalian subject to a remote receiver unit, comprising a signal input for receiving the signal from a remote physiological sensor, an output device for transmitting the signal to the remote unit, and a signal processor for relaying the signal from the signal input to the output device, wherein the signal processor comprises one or more receivers each receiver adapted to handle a specified signal carrier frequency.

Preferably, first and second receivers are provided within the signal processor which first and second receivers are operable to handle different carrier frequencies. Alternatively, the first and second receivers are operable to handle the same carrier frequency.

The signal transfer unit can comprise a signal input having a first and second antenna and the signal processor can comprise a switch to ensure that the more usable signal from one of the first and second antenna is processed by the signal processor and output therefrom to the output device.

Preferably, the signal input comprises three or more antennae and the signal processor comprises a device for hunting between each of the three or more antennae to determine which antenna is receiving the most usable signal.

Preferably, the signal processor comprises a digital signal processor programmable to effect one or more virtual receivers for the signal.

According to another aspect of the invention there is provided a portable signal transfer unit for relaying a signal representative of physiological data of a mammalian subject to a remote receiver unit, comprising a signal input for receiving the signal from a remote physiological sensor, wherein the signal is in the form of a digitally modulated carrier frequency, an output device for transmitting the signal to the remote unit, and a signal processor for transferring the digital signal to the output device, further comprising a controller having a stored execution program for the digital signal processor and being operable to transfer the execution program to the digital signal processor when the portable signal transfer unit is initiated at start up.

A yet further aspect of the invention provides a signal transfer unit for relaying a signal representative of physiological data of a mammalian subject to a remote receiver unit, comprising a signal input for receiving the signal from a remote physiological sensor, an output for transmitting the signal to the remote unit, a controller for operably communicating the signal between the signal input and output device, and a physiological sensor which operably provides data representative of a physiological parameter of the subject to the controller in use, whereby the controller in turn incorporates the data into the signal for subsequent transmission by the output device.

In one embodiment, the signal transfer unit comprises an interface such as an RS 232 port to enable communication between the controller and a physiological sensor.

Also, it is possible for the physiological sensor to be incorporated within the signal transfer unit. The physiological sensor can comprise one or more of a motion sensor such as an accelerometer, a position sensor such as a mercury switch enabling determination of whether the subject is upright or lying down for example, and/or a microphone for monitoring the subject's breathing sounds.

A yet further aspect of the invention provides a portable signal transfer unit for relaying a signal representative of physiological data of a mammalian subject to a remote receiver unit, comprising a signal input for receiving the signal from a remote physiological sensor, a memory for buffering the signal, an output device for transmitting the signal to the remote unit, and an indicator for indicating to the subject whether the signal transfer unit is within range of the remote unit to enable effective transmission of the signal from the signal transfer unit to the remote unit. Preferably, the signal transfer unit comprises a communication port for communicating with the remote unit. The communication port can comprise the output device adapted to receive signals from the remote unit. Beneficially, the remote unit can be powered using mains electricity and can therefore generate a stronger signal than the signal transfer unit. Accordingly, the remote unit can be configured to send a signal to the signal transfer unit to indicate whether or not a satisfactory signal is being received by the remote unit from the signal transfer unit.

BRIEF DESCRIPTION OF THE DRAWINGS

A description of a preferred embodiment of the invention will now be described, by way of example only, with reference to the accompanying drawings, in which.

DETAILED DESCRIPTION OF THE PRESENTLY PREFERRED EMBODIMENTS

Figure 1:
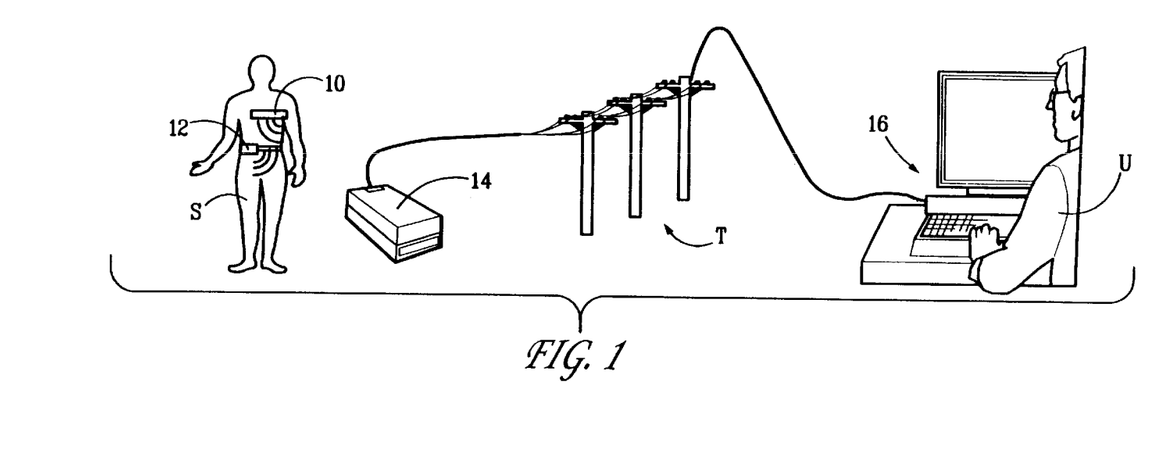
FIG. 1 is a schematic drawing of a physiological monitoring system incorporating a signal transfer unit according to the invention.

FIG. 1 illustrates a physiological sensor device or array 10 according to the invention which is attached to the chest of a human subject or patient S. Device 10 comprises an array of sensors 10a (to be described later), which generate data about the physiological condition of the subject. This data is transmitted to a portable signal transfer unit 12. In turn, signal transfer unit 12 transfers a signal representative of the measured physiological parameters to a base station 14 which operably communicates with a remote monitoring station 16, which can comprise a suitably programmed computer 16b for example, via a telemetry or telephonic link T, such as a land based telephone system for example, using modems 14c and 16a.

Figure 2:
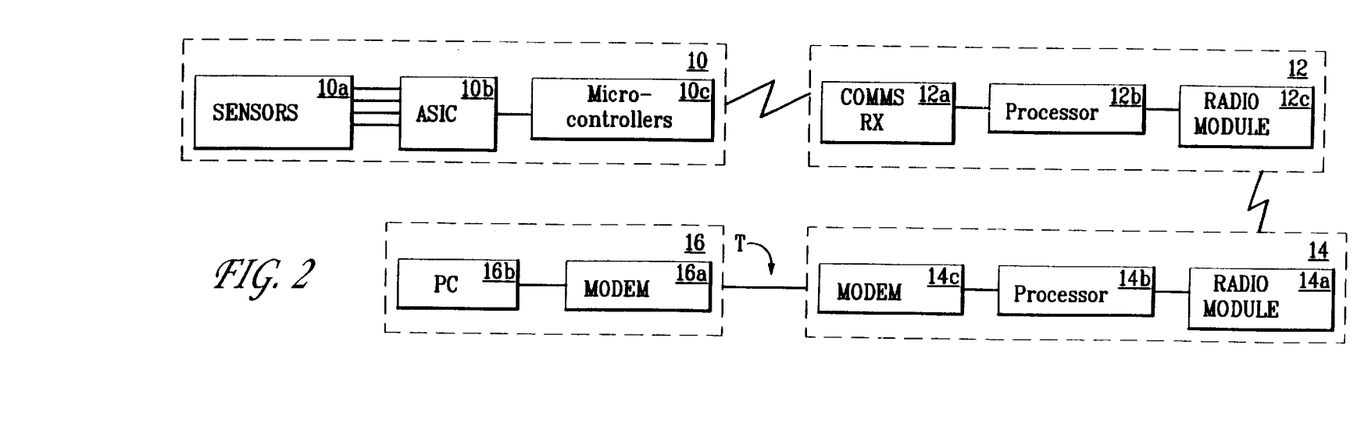
FIG. 2 is a schematic block diagram of the components of the different parts of the system shown in FIG. 1.

The basic structure of the different components in the system is shown in a schematic block diagram in FIG. 2. As can be seen, device 10 comprises an array of sensors 10a in communication with suitable electronics forming a controller for processing and communicating physiological data to the signal transfer unit 12. In this example, device 10 comprises an application specific integrated circuit (ASIC) 10b, and at least one micro-controller 10c. Further details of the preferred form of electronics and details of the sensors are described below, while further details of the structure and method of manufacture of the device 10 are given in our co-pending patent applications entitled "Physiological Sensor Array", U.S. patent application Ser. No. 09/292,159 (Attorney Reference No. NEXT-0004) and "Physiological Sensor Device", U.S. patent application Ser. No. 09/292,157 (Attorney Reference No. NEXT-0005), the contents of which are incorporated herein by reference in their entireties.

As will be explained in detail herein, the system further comprises a portable signal transfer unit 12 having a receiver 12a in communication with a processor 12b which in turn enables two-way transfer of data and commands to base station 14 via a radio module 12c.

Base station unit 14 comprises a radio module 14a for receiving data signals from signal transfer unit 12, a processor 14b suitably programmed to manipulate the physiological data and to enable transfer from base station 14 to remote monitoring station 16 via a modem 14c and a link T. Remote monitoring station 16 can comprise a modem 16a and programmable computer 16b for example. Further details of the base station 14 and remote monitoring station 16 as well as the system as a whole, including details of the format of transmitted data and transmission protocols between the device 10 and signal transfer unit 12, are given in our co-pending application entitled "Portable Remote Patient Telemonitoring System", U.S. patent application Ser. No. 09/292,405 (Attorney Reference No. NEXT-0002), which is incorporated herein by reference in its entirety.

Figure 5:
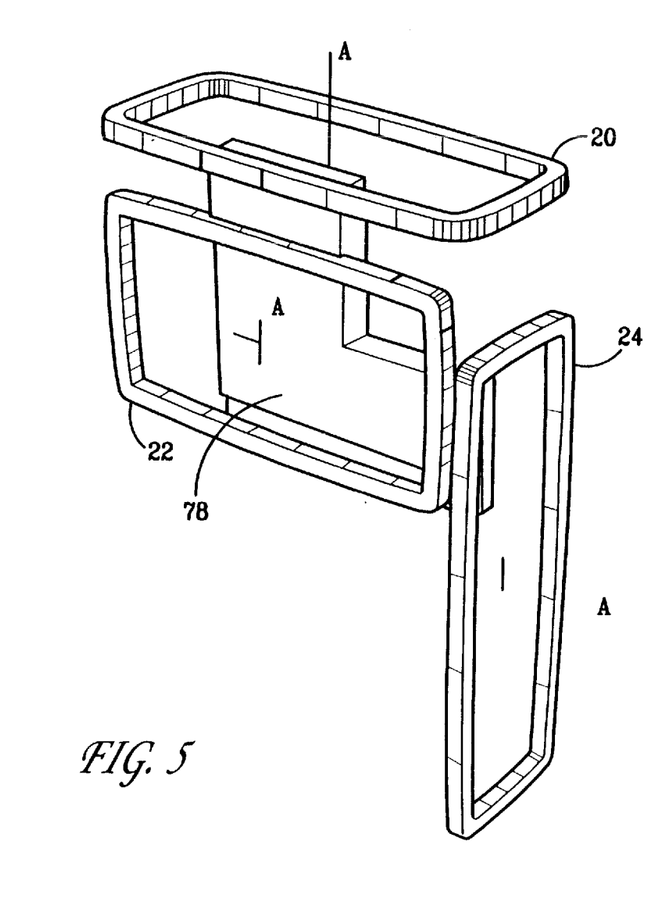
FIGS. 5 and 6 are schematic perspective views of an orthogonal coil arrangement and user interface for a signal transfer unit according to the invention.

The signal transfer unit 12 is designed to be locatable near a physiological sensor device 10 locatable on the chest or other part of a mammalian subject. Accordingly, a suitable location is on a belt around a patient's waist. The signal transfer unit 12 acts to receive physiological data from the sensor device 10, preferably in a unidirectional manner thereby enabling use of a receiver without capacity or need for transmission. The components of signal transfer unit 12 are shown in greater detail in FIG. 3. In the preferred embodiment, the front end receiver comprises a coil assembly having three orthogonal coils 20, 22 and 24. As shown in FIG. 5, each coil is maximally sensitive to magnetic fields parallel to an axis A approximately perpendicular to the coil and wherein each of coils 20, 22 and 24 are preferably arranged orthogonally such that each of axes A is oriented at substantially 90° with respect to each of the other axes.

The coils act like secondary coils loosely coupled in a transformer arrangement with the emitter coil of a sensor 10 acting as the primary. The coils are linked to a receiver 26 for filtering and amplifying an incoming signal as well as conducting analogue to digital conversion before passing the signal on to a digital signal processor, DSP 28. The DSP can be a Motorola 56303 device, for example. In turn, the signal from the DSP 28 is fed to a controller such as a Hitachi micro-controller H8/3048 device labeled 30 in FIG. 3.

Figure 3:
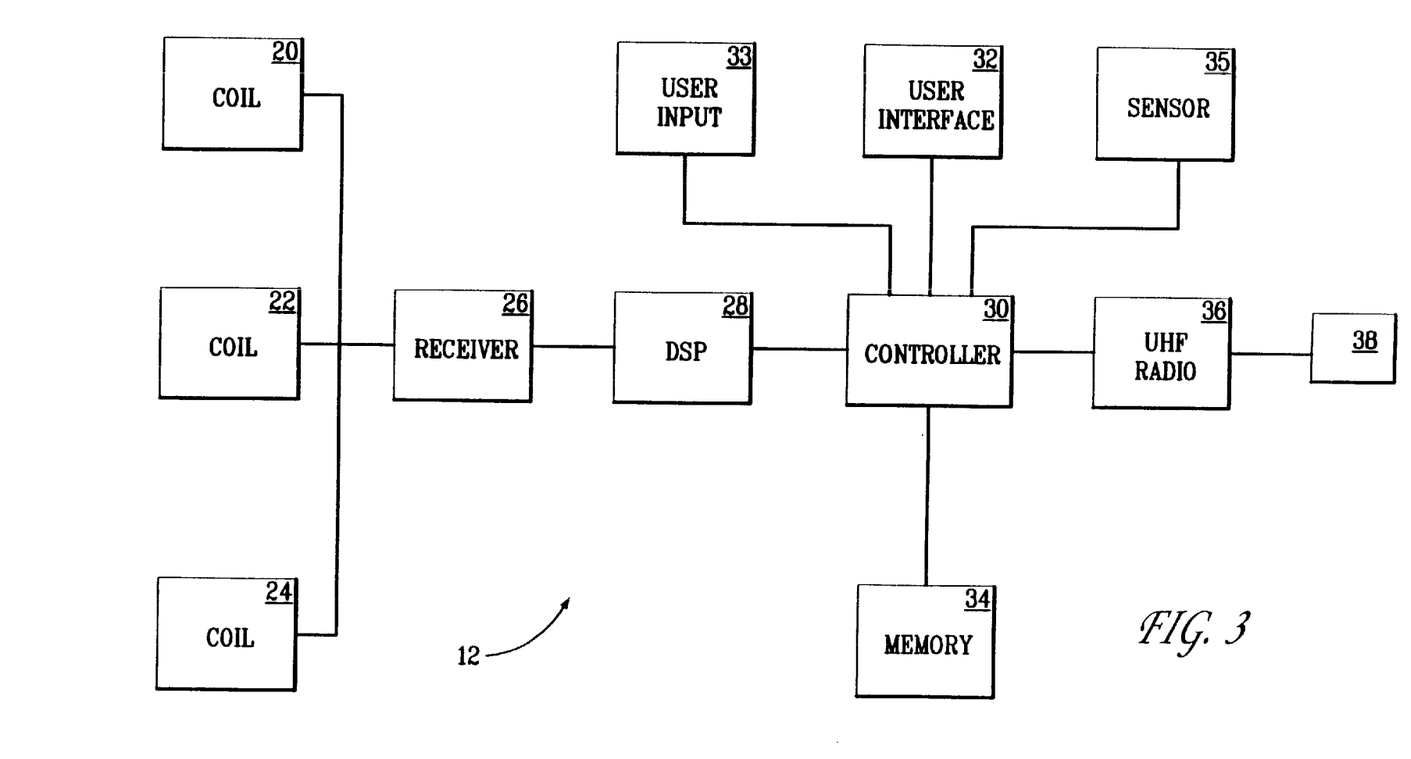
FIG. 3 is a schematic block diagram of the components forming part of signal transfer unit according to the invention.

Controller 30 operably communicates with a user interface 32 and a buffer storage memory 34. The controller 30 acts to interface the DSP 28 with a UHF radio 36 and radio antenna 38 for transmission of physiological data to base station 14. UHF radio 36 also acts to receive signals including commands from base station 14. Beneficially, signal transfer unit 12 also comprises a user input 33 such as an RS 232 interface thereby enabling communication of further data to controller 30. For example, input 33 can be used to incorporate further sensors into the system such as a pulse oximeter, data from which can be incorporated by controller 30 into the signal transmitted at antenna 38 as appropriate.

Indeed, it is possible to incorporate physiological sensors within signal transfer unit 12. A suitable sensor 35 operably communicates with controller 30 and, for example, sensor 35 can comprise a position sensor within the signal transfer unit. The position sensor might comprise a mercury switch to indicate whether the subject is standing up or lying down. Also, a movement sensor can be provided comprising an accelerometer for example. Also, sensor 35 can comprise a microphone which might detect lung sounds from the subject. Again, the data from the one or more sensors 35 is operably communicated to controller 30 and incorporated into the signal for transmission by antenna 38 as appropriate.

Figure 4:
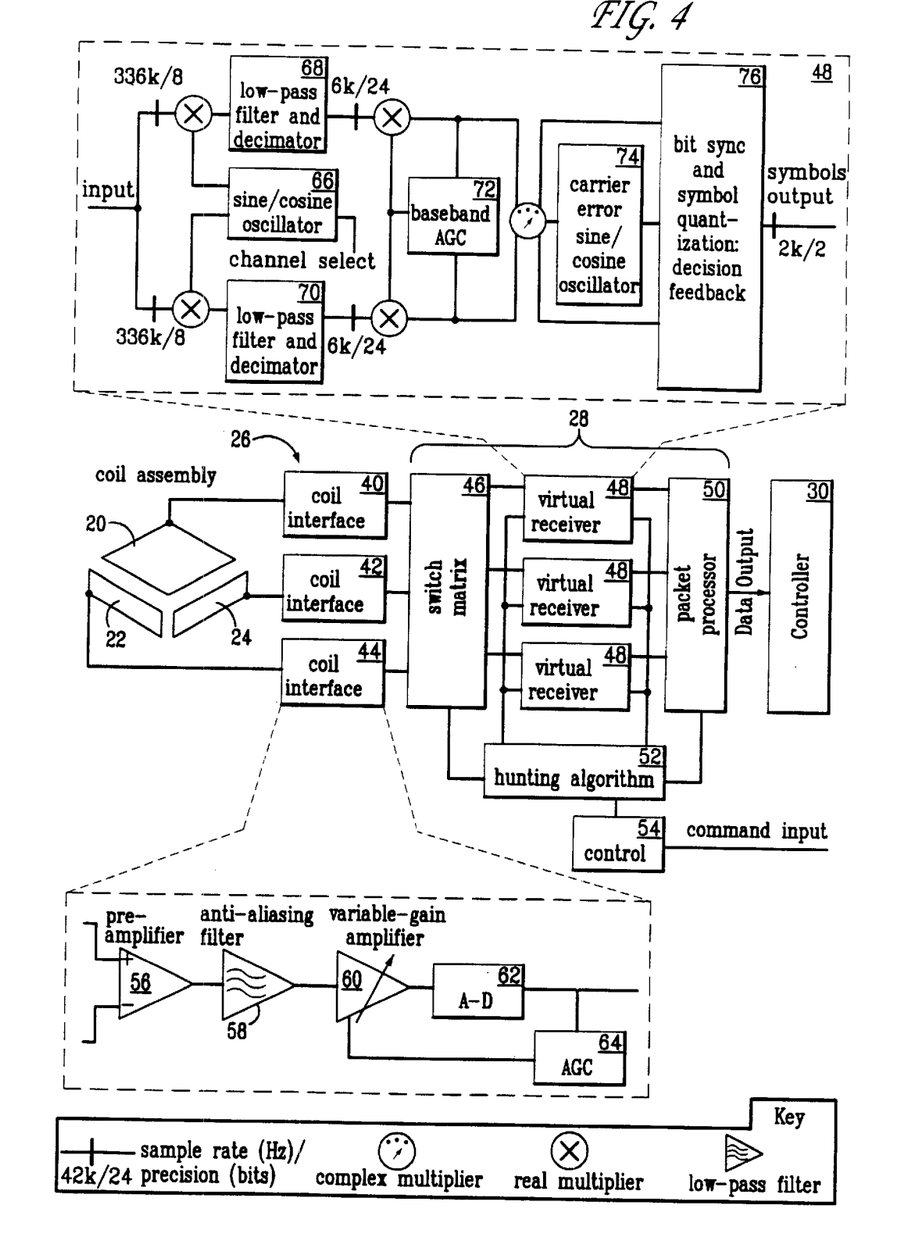
FIG. 4 is a schematic block diagram of pail of the unit shown in FIG. 3.

Referring to FIG. 4, a schematic representation of part of the system shown in FIG. 3 is given wherein each of coils 20, 22 and 24 has an associated coil interface, 40; 44 and 42 respectively, within receiver 26. The coil interfaces 40, 42 and 44, can be seen to comprise the components of the receiver 26 specified in FIG. 3. Accordingly, a pre-amplifier 56 is connected to an associated coil, and the signal from this is passed through an anti-aliasing filter 58 and on to a variable gain amplifier 60. Analog to digital conversion is carried out by an A/D converter 62. All of these features can be provided in the form of hard wired circuitry on a suitably located printed circuit board within signal transfer unit 12. Preferably an automatic gain control (agc) 64 is provided between the output of A/D converter 62 and variable gain amplifier 60. AGC 64 can be implemented in software in the DSP 28.

Typically receiver 26 would be expected to perform well with a 14 microvolt rms signal which might suitably be derived from an inductance coil transmitter located on sensor device 10 within about one meter of signal transfer unit 12. The amplifier device 56 can for example be a one section is an LM 6134 device which has suitable low input noise. Additionally, it is important to improve input signal to receive 26 by using a suitable large number of turns on each of the receiving coils subject to limiting the self resonant frequency of the coil to above the range of interest. Further factors in improving the signal are to reduce circuit noise for example by screening the components and especially the coils 20, 22 and 24 should be screened from other electrical components as described later.

The coil interfaces each lead to a switch matrix 46 which connects the appropriate coil 20, 22 or 24 to one of the virtual receivers 48 which communicates with packet processor 50. The virtual receivers 48 can be of any number as described later.

A hunting algorithm 52 is programmed in DSP 28 to monitor the signal at packet processor 50 and to hunt between the two unused coils at any one given time in order to determine if one of the other two coils is receiving a stronger signal or signal which decodes better to attempt to communicate error free physiological data, from the relevant physiological sensor device 10. That is, due to the subject adopting different positions throughout the day such as lying down while sleeping or being somewhat curled up in a sitting position, the strength of signal from any given physiological sensor device 10 located somewhere on the subject's body, can be different at the coils 20, 22 and 24. In one form, a single virtual receiver 48 can be implemented in software for receiving the signal from a sensor device 10 via the selected coil. Coil selection can take place using a second virtual receiver 48 programmed to look at the signals from the other two coils in order to determine if one coil provides a better signal. In another form, three virtual receiver 48 are used for a given carrier frequency each coupled to one of the coil antennae enabling software selection of the appropriate virtual receiver 48 to be used according to the quality of signal from the associated coil antenna. The packet processor 50 demodulates the signal and provides a serial link to a signal processing unit, that is controller 30.

When multiple input carrier frequencies are used they are preferably separated by a suitable frequency spacing greater than the carrier band width to reduce interference between channels. In a preferred form a channel spacing of about 6 kHz is used for a 4 kHz band width channel. Also in a preferred form, the option of several and preferably 16 channels is provided between carrier frequencies of 54 kHz through to 144 kHz. However, where larger amounts of data are to be carried by signal transfer unit 12, data compression could be used and/or greater band width might be required. For example, a three lead ECG monitor might preferably use an 8 kHz band width of compressed data. Accordingly, the channel separation might be 10 kHz. That is, a channel spacing of slightly greater than the band width is used to reduce interference. Indeed, it is not necessary to use a fixed separation between channels and accordingly, the separation might be variable depending on the rate or amount of data transfer required.

Beneficially, the DSP 28 can be pre-programmed to expect signals on specified channels and for example a specified type of sensor device 10 can be manufactured to emit at a predetermined frequency such as 54 kHz such that the portable signal transfer unit 12 can be programmed to expect a signal on the associated, in this case 54 kHz, channel. Accordingly, when two or more sensor devices are used then the DSP 28 can accordingly be programmed to expect signals on the relevant channels.

Accordingly, in the above configuration if say a single sensor device 10 is used which is emitting at a predetermined frequency of say 54 kHz, then the DSP 28 is programmed to have a first virtual receiver channel at 54 kHz for receiving the signal from the selected coil, and at least a second programmed virtual receiver 48 for hunting between the other two coils to enable determination of the most usable signal. Where all 16 channels are used then the DSP 28 can be programmed to have 32 virtual receiver channels, two for each frequency, one for use and one for hunting, or in another form, three for each frequency thereby to avoid use of the hunting process 52 between the unused coils as described above.

Control 54 can be used to govern various aspects of the receiving algorithm, for example, channel selection. Control 54 can be actuated on the command input from controller 30.

Further detail of the nature of the virtual receiver 48 is shown in FIG. 4 whereby the virtual receiver 48 can be seen to accept a digital signal at say 336 kilo samples per second (ksps) with a precision of 8 bits. The specific form of data handling described here assumes that the data transmitted from a physiological sensor device 10 is in the form of a quadrature phase shift keyed carrier frequency.

The input signal is passed through a pair of real multiplier whose other inputs are derived from a sine/cosine oscillator 66. The output from the real multiplier is passed to low pass filter and decimator 68 and 70, the output from which are two 6 ksps signal each having a precision of 24 bits. Each of the signals emitted by filter and decimators 68 and 70 passes through a second pair of real multiplier whose other inputs are derived from a base band automatic gain control (AGC) 72. The signal are subsequently fed to a complex multiplier whose other inputs is deriver from a carrier error sine/cosine oscillator 74 which is controller by bit synchronization and symbol quantization decision feedback device 76 whose input are derived from the outputs of the complex multiplier. Subsequently data is output to the packet processor 50 in a form of a 2 ksps signal having 2 bits precision. The virtual receiver 48 is implemented in software in the DSP 28. The DSP 28 to controller 30 interface comprises three signals, the first a framing pulse to indicate the first bit within a packet, the second a clock signal and the third a serial data signal with the least significant bit (LSB) first. A suitable protocol for communication includes a frame of data comprising 160 bits, having a data field of 128 bits and a time stamping field of 14 bits. Each channel (for each physiological sensor device 10) can have a data mate of approximately 4 vkbps thus allowing for 25 frames per second per channel. This allows 25×128 data bits per second which equals 3200 data bits second per channel.

The number of channels carried by this link in the final product is preferably no greater than 3, resulting in a bit-rate of 12 kbps and a data rate of 9.6 kbps. Of course, the number of channels can be limited to one, where a single sensor device 10 is used.

Physically, the interface operates using an interrupt regime and a DMA controller. The frame alignment signal will drive an interrupt in the H8/3048; this interrupt will be capable of waking the microprocessor 30 out of a software standby mode when it is in a state of power saving.

In another application, it is possible for the data stream from the DSP 38 to not continuous thus allowing the controller 30 to have long enough spells of inactivity to go into a software standby mode to save power and achieve a long battery life. Alternatively the stream can be continuous, with many of the frame packets potentially being empty.

The incoming data frame will have the CRC status bits examined and if these show that the data is valid, the data is extracted and depending on the status of the signal transfer unit 12 to base station 14 radio link, this information can either be directly built into a packet for transmission to the base station, or placed in a buffer ready for this, or will be sent to the next available area of a storage memory 34. Accordingly, on-chip buffers can be provided for temporary storage and a memory 34 such as a DRAM, FLASH or other memory device can be used for larger amounts of data ready for transfer to base station 14.

The transceiver forming the UHF radio 36 can be based on the RF2905 transceiver chip. The following interface lines are preferably present to the base-band:

data in (data received from the base station 14)

data out (data transmitted to the base station 14)

T/R—transmit/receive switch power up flag (to wake the RF2905 from sleep mode)

The other interface connections to the RF2905 chip 36 can be derived from these using a small amount of logic circuitry; this reduces the number of I/O ports required on the processing device 30.

The link between signal transfer unit 12 and station 14 preferably runs at 40 kbps baud rate. A packet can typically comprise of preamble, a synchronization codeword, various packet definition codes, a packet ID, data and a CRC error detection code. The CRC code can be 16 bits wide, and the data content within a packet can be 32 bits. This results in the CRC algorithm performing over a 48 bit packet.

Data received from the TxRx is preferably asynchronous. Clock extraction is therefore a function that must be performed by the signal transfer unit 12. This involves over-sampling of the synchronization codeword (a 101010. . . pattern). Also, frame alignment must be performed. The CRC should be performed in the signal transfer unit 12 for both the transmitted and received data. The incoming data from the radio is preferably connected to a hardware interrupt on the controller 30. The CRC algorithm can be performed in real-time, utilizing 32 bit registers and various rotate and shift instructions in the processor 30 instruction set. If the CRC is not performed in real-time, the data can be buffered and the CRC can be performed as soon as the current reception is complete. Due to the base station channel being predominantly for reverse traffic (data to the base station), this incoming data procedure has little activity compared to the forward direction (data from the base station), this is not the case however during periods of poor reception when data needs to be re-transmitted and error codes are sent regularly from the base station.

It is noted that at start up controller 30 can be programmed to initialize and transfer an execution program across to DSP 28.

Figure 6:
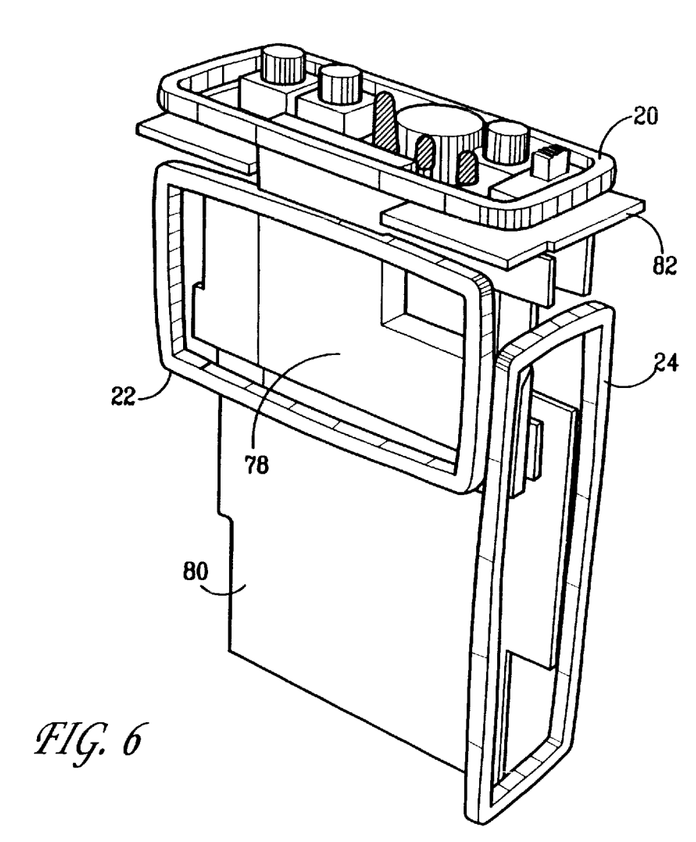

Physically, the portable signal transfer unit 12 is preferably quite small and lightweight. For example dimensions in the order of 115×65×25 mm are appropriate. Additionally, lightweight batteries such as four AA cells are preferably used to power the system. In order to maximize signal reception the orthogonal coils 20, 22 and 24 preferably are quite large and make optimum use of the interior cavity of a casing for the portable signal transfer unit 12. A suitable arrangement is shown in FIG. 5 wherein a first coil 20 is locatable below the top cover adjacent the user interface display panel. The second coil 22 is preferably locatable adjacent a side panel of the device and similarly third coil 24 is locatable against an edge panel. The coils can be arranged about a central support member 78 to which two printed circuit boards 80 and 82 are attachable as shown in FIG. 6. Printed circuit board 80 can carry a majority of the electrical components described earlier while printed circuit board 82 preferably carries some electrical components as well as user interface components such as LEDs, switches and a buzzer as described later.

Figure 7:
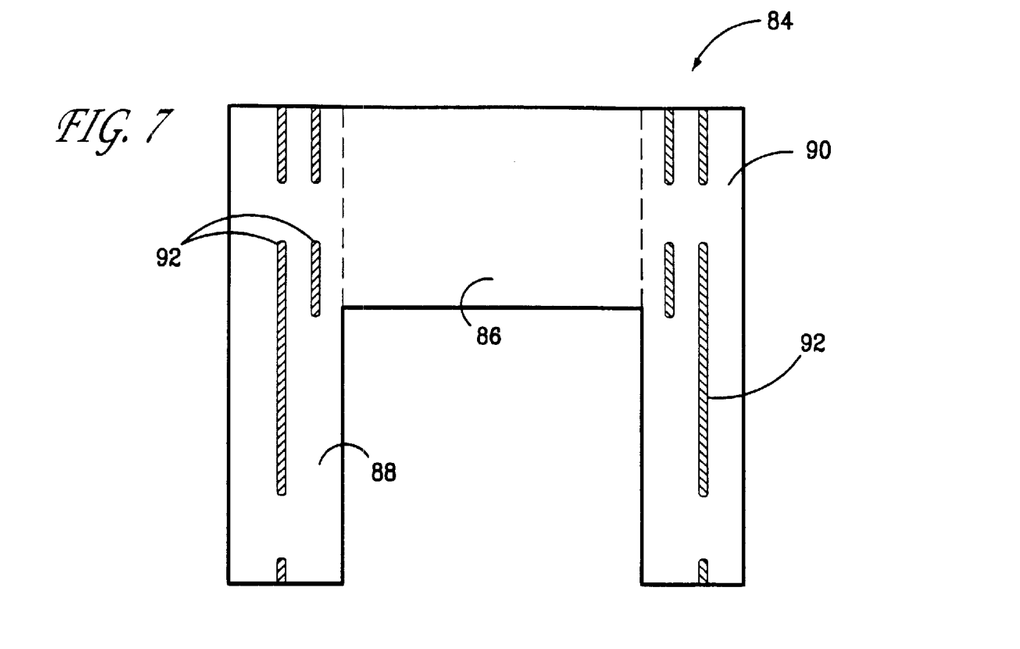
FIG. 7 is a schematic of a screening plate with fold lines marked for use in the unit shown in FIGS. 5 and 6.

Printed circuit board 82 provides screening for coil 20. Additionally, a further screening element is preferably used. In a preferred form a screening plate 84 of a suitable electrically conductive material such as tin plate is used. Plate 84 comprises a central portion 86 having dimensions substantially the same as the outer dimensions of coil 22. The edges of central portion 86 are connected to two side portions 88 and 90 which are folded through 90° along the edges of central portion 86 to enable side portion 90 to be located on the inside of coil 24 when central potion 86 is located on the inside of coil 22. As can be seen FIG. 7, slots 92 are provided to enable location of plate 84 against the receiver printed circuit broad and printed circuit board 80. The cells can be located below coil 22 within signal transfer unit 12.

Additionally, radio frequency antenna 38 is locatable within signal transfer unit 12. Preferably, the antenna comprises a conductive plate antenna, for example, consisting of the conductive track on a printed circuit board. Preferably the size of the conductive plate can be in the order of 90 to 110×40 to 60 mm. Preferably, the antenna is locatable against an inside surface of units 12. More preferably the antenna is locatable against the surface which is positioned adjacent the subject in use, for example, adjacent a surface carrying a clip for attachment to a subject's belt or clothing. Alternatively, the antenna could be external and for example comprise a stub antenna.

Figure 8:
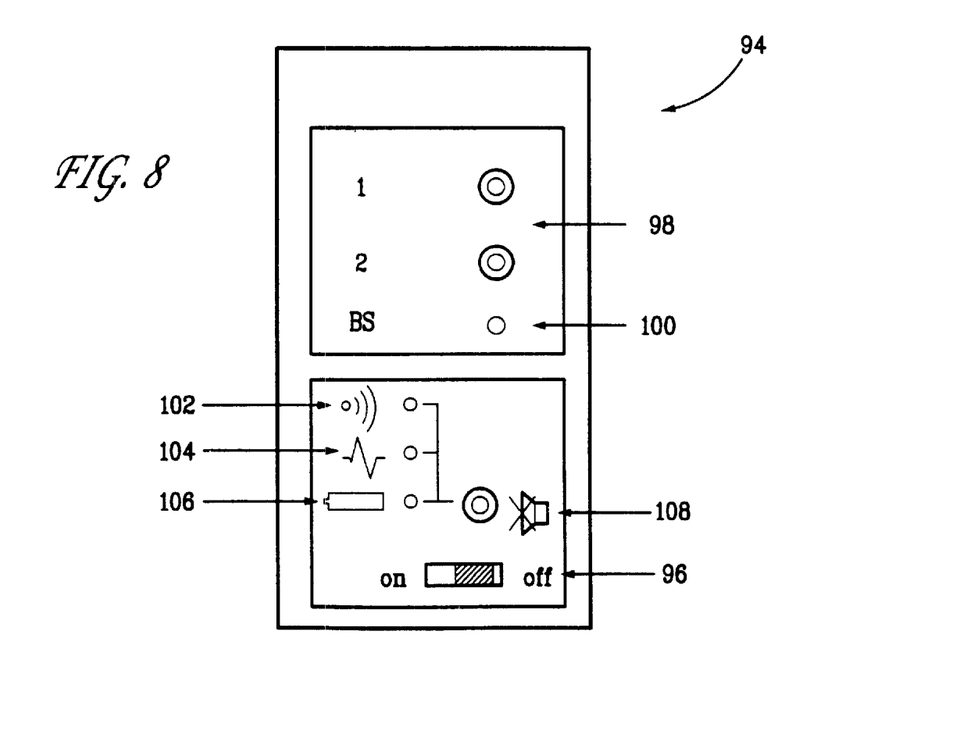
FIG. 8 is a schematic diagram of the user interface of the signal transfer unit according to the invention.

Referring now to the user interface 94 shown in FIG. 8, a user is preferably provided with an on/off switch 96. Additionally, preferably two event buttons 98 are preferably provided. One of the event buttons can be used to identify a particular event such as taking medication and the other for example to indicate that the subject is feeling a particular pain. Indeed, the nature of the events for each of the event buttons can be agreed between a clinician and individual patient. Of course actuation of either button is noted by controller 30 and an appropriate flag placed in the data at the relevant time to indicate which button was pressed.

Preferably a device is provided to indicate to the user that they are to go to the base station 14 to receive a message displayed on the base station 14 or otherwise to perform a specified function which may be predetermined and agreed with the patient. Such an indicator device can comprise an LED 100 and also an audible sound might be emitted from a buzzer. The nature of the events to be performed by the patient when LED 100 is lit might be for example to perform an auxiliary sensor measurement such as measuring weight, taking the patient's blood pressure or other appropriate action.

Additionally, a series of warning indicators are preferably provided. An LED 102 can be used to indicate when the portable signal transfer unit 12 is out of range of the base station 14. Preferably, the LED flashes when signal transfer unit 12 is out of range. Additionally, LED 112 can be turned on continuously when the memory 34 is filled to a predetermined level such as 90% thereby to indicate to the subject that it is necessary to move within range of the base station 14.

Preferably an LED 104 is provided to indicate that the signal transfer unit 12 cannot detect a signal from an anticipated sensor device 10. Accordingly, the patient is required to check that the signal transfer unit 12 is not too far away from device 10. By moving the signal transfer unit 12 closer to a device 10, the patient is able to determine if in fact the error is likely to be that the power for device 10 has run out in which case it is necessary to replace the sensor device 10.

Additionally, an LED 106 is preferably provided to indicate the power status of the battery power source for signal transfer unit 12. Preferably LED 106 flashes under normal use but lights up continuously when the batteries are running low.

Preferably a buzzer is activated at a change of status of any of LEDs 100, 102, 104 and 106. Accordingly, a switch 108 is preferably provided to silence the buzzer once the user has identified which warning LED has been activated.

Beneficially a simple but sufficient array of user interface devices can be provided which fit within a preferred space and power consumption requirements which enable the portable signal transfer unit to be compact and energy efficient thereby to increase output of use and useable life with a given set of batteries. The energy efficiency is also derived from the preceding description of the preferred form of electronic controls which receive, process and store data ready for transmission to base station 14. For example a maximum power consumption of 60 mA at 3 V from 4 AA cells is preferred.

Although an exemplary embodiment of the invention has been described in detail above, those skilled in the art will readily appreciate that many additional modifications are possible in the exemplary embodiment without materially departing from the novel teachings and advantages of the invention. All such modifications are intended to be included within the scope of this invention as defined in the following claims.

What we claim is:

1. A portable signal transfer unit for relaying a signal representative of physiological data of a mammalian subject from a remote physiological sensor to a remote receiver unit, comprising an input device which operably receives the signal through a wireless transmission from the remote physiological sensor, said input device comprising at least two antennae for receiving the signal from a transmitter on the remote physiological sensor, a signal processor which selects an output signal of one of said at least two antennae having a more usable signal for processing, and an output device that receives the selected output signal from said signal processor and wirelessly transmits the selected output signal to the remote receiver unit.

2. A portable signal transfer unit according to claim 1 wherein said at least two antennae comprise three antennae and each of the three antennae has a principal reception plane wherein the reception plane of the three antennae are substantially orthogonally arranged with respect to each within the unit.

3. A portable signal transfer unit according to claim 1 wherein the antennae are inductively coupled with a transmission coil of the transmitter on the remote physiological sensor.

4. A portable signal transfer unit according to claim 3 wherein the antennae comprise three orthogonally arranged coils.

5. A portable signal transfer unit according to claim 1 wherein the output device comprises a stub antenna.

6. A portable signal transfer unit according to claim 1 wherein the output device comprises a plate antenna.

7. A portable signal transfer unit according to claim 6 further comprising an outer casing and wherein the plate antenna has a surface area substantially equal to the surface area of the largest face of the outer casing.

8. A portable signal transfer unit according to claim 7 wherein the plate antenna is positioned adjacent the wall of the outer casing adapted to be adjacent the subject in use.

9. A portable signal transfer unit according to claim 8 wherein the wall adapted to be positioned adjacent the subject in use comprises a clip attachable to a belt on the subject.

10. A portable signal transfer unit according to claim 6 wherein the plate antenna comprises a conductive track on a non-conductive substrate.

11. A portable signal transfer unit according to claim 1 comprising a second input device enabling communication with a controller in the remote receiver unit.

12. A portable signal transfer unit according to claim 11 wherein the second input device comprises a transceiver enabling both input and output signals.

13. A portable signal transfer unit according to claim 11 wherein the second input device comprises an RF receiver.

14. A portable signal transfer unit according to claim 1 having a user interface comprising at least one of an on/off switch adapted to remove or enable power supply to the unit, an indicator to indicate the status of the power supply to the unit, an indicator to indicate whether a signal is being received from the physiological sensor device, an indicator to provide an indication of whether the unit is within range of the remote unit, an audible alarm operable upon command from the remote unit, and a switch to enable the user to deactivate the user output when appropriate.

15. A portable signal transfer unit according to claim 1 wherein the signal processor comprises at least two receivers for handling specified signal carrier frequencies received by said at least two antenna.

16. A portable signal transfer unit according to claim 1 comprising an on-board electrical power source for all electrical components within the portable signal transfer unit.

17. A portable signal transfer unit according to claim 1 further comprising a memory adapted to enable buffering of the signal for several minutes.

18. A portable signal transfer unit according to claim 17 wherein the memory is adapted to enable buffering of the signal for at least 30minutes.

19. A portable signal transfer unit according to claim 1 wherein a first and second receiver are provided within the signal processor which first and second receivers are operable to handle different carrier frequencies.

20. A portable signal transfer unit according to claim 1 wherein a first and second receiver are provided within the signal processor which first and second receivers are operable to handle the same carrier frequency.

21. A portable signal transfer unit according to claim 1 wherein the input device comprises a first and second antenna, and the signal processor comprises a switch to ensure that the more usable signal from one of the first and second antennae is processed by the signal processor and output therefrom to the output device.

22. A portable signal transfer unit according to claim 1 wherein the input device comprises three antennae and the signal processor comprises a device for hunting among each of the three antennae to determine which is receiving the most usable signal.

23. A portable signal transfer unit according to claim 1 wherein the signal processor comprises a digital signal processor adapted to process digitally encoded signals received from the input device.

24. A portable signal transfer unit for relaying a signal including ECG data of a mammalian subject from a remote physiological sensor to a remote receiver unit, comprising an input device which operably receives the signal through a wireless transmission from the remote physiological sensor, an output device that wirelessly transmits the signal to the remote receiver unit, a controller for operably communicating the signal between the input device and the output device, and another physiological sensor connected to said controller so as to operably provide data representative of another physiological parameter of the subject to the controller in use, whereby the controller in turn incorporates physiological data relating to the another physiological parameter into the signal for subsequent transmission by the output device to the remote receiver unit.

25. A portable signal transfer unit according to claim 24 comprising an interface which enables connection of the physiological sensor that provides the another physiological parameter to the controller.

26. A portable signal transfer unit according to claim 24 wherein the physiological sensor that provides the another physiological parameter is incorporated within a housing of the signal transfer unit.

27. A portable signal transfer unit according to claim 24 wherein said physiological sensor comprises a motion sensors.

28. A portable signal transfer unit according to claim 27 wherein said motion sensor comprises an accelerometer.

29. A portable signal transfer unit according to claim 26 wherein said physiological sensor comprises a position sensor.

30. A portable signal transfer unit according to claim 29 wherein said position sensor comprises a mercury switch that detects the relative orientation of the unit and hence subject in use.

31. A portable signal transfer unit according to claim 26 comprising a microphone for monitoring sounds within the vicinity of the subject.

32. A portable signal transfer unit according to claim 24 wherein the signal received by the input device is in the form of a digitally modulated carrier frequency, further comprising a digital signal processor that demodulates the signal from the digitally modulated carrier frequency and provides the demodulated signal to the controller.

33. A portable signal transfer unit according to claim 32 wherein the controller is programmed to initialize and to transfer an execution program to the digital signal processor when the portable signal transfer unit is initiated at start up.

* * * * *